US00PP31872P2

(12) United States Plant Patent
Wouters

(10) Patent No.: US PP31,872 P2
(45) Date of Patent: Jun. 16, 2020

(54) ***EUONYMOUS* PLANT NAMED 'WHITE SPIRE'**

(50) Latin Name: *Euonymous japonicus*
Varietal Denomination: WHITE SPIRE

(71) Applicant: Green Beheer BV, St. Oedenrode (NL)

(72) Inventor: Theo Wouters, St. Oedenrode (NL)

( * ) Notice: Subject to any disclaimer, the term of this patent is extended or adjusted under 35 U.S.C. 154(b) by 0 days.

(21) Appl. No.: 16/501,508

(22) Filed: Apr. 18, 2019

(51) Int. Cl.
*A01H 5/12* (2018.01)
*A01H 6/00* (2018.01)

(52) U.S. Cl.
USPC ..... Plt./246

(58) Field of Classification Search
USPC ..... Plt./246
CPC ... A01H 5/12; A01H 5/02; A01H 5/00; A01H 6/00
See application file for complete search history.

(56) References Cited

PUBLICATIONS

Floral Daily 2018 Plenty of Plantipp novelties at Plantarium [online] retrieved on Nov. 21, 2019, retrieved from the Internet at https://www.floraldaily.com/article/9016748/plenty-of-plantipp-novelties-at-plantarium/, 12 pp. (Year: 2018).*

Screen captures from YouTube video clip entitled "*Euonymus* White Spire," 4 pp. uploaded on Nov. 21, 2019 by user "jhwu" retrieved from the Internet at https://www.youtube.com/watch?v=ty0zGcGx2YM. (Year: 2018).*

Upov Pluto Plant Variety Database Nov. 19, 2019 [online] retrieved on Nov. 21, 2019, retrieved from the Internet at https://www3.wipo.int/pluto/user/en/index.jsp, one page. (Year: 2019).*

* cited by examiner

*Primary Examiner* — June Hwu
(74) *Attorney, Agent, or Firm* — Cassandra Bright

(57) ABSTRACT

A new and distinct *Euonymous* cultivar named 'WHITE SPIRE' is disclosed, characterized by stable, variegated foliage having green, yellow-green, white, greyed-green and green-white marbling, and an upright, columnar, dense, neat habit. Plants are very well suited for performance in the landscape, including as a specimen plant or a hedge. The new cultivar is an *Euonymous*, suitable for ornamental garden purposes.

2 Drawing Sheets

Figure 1:
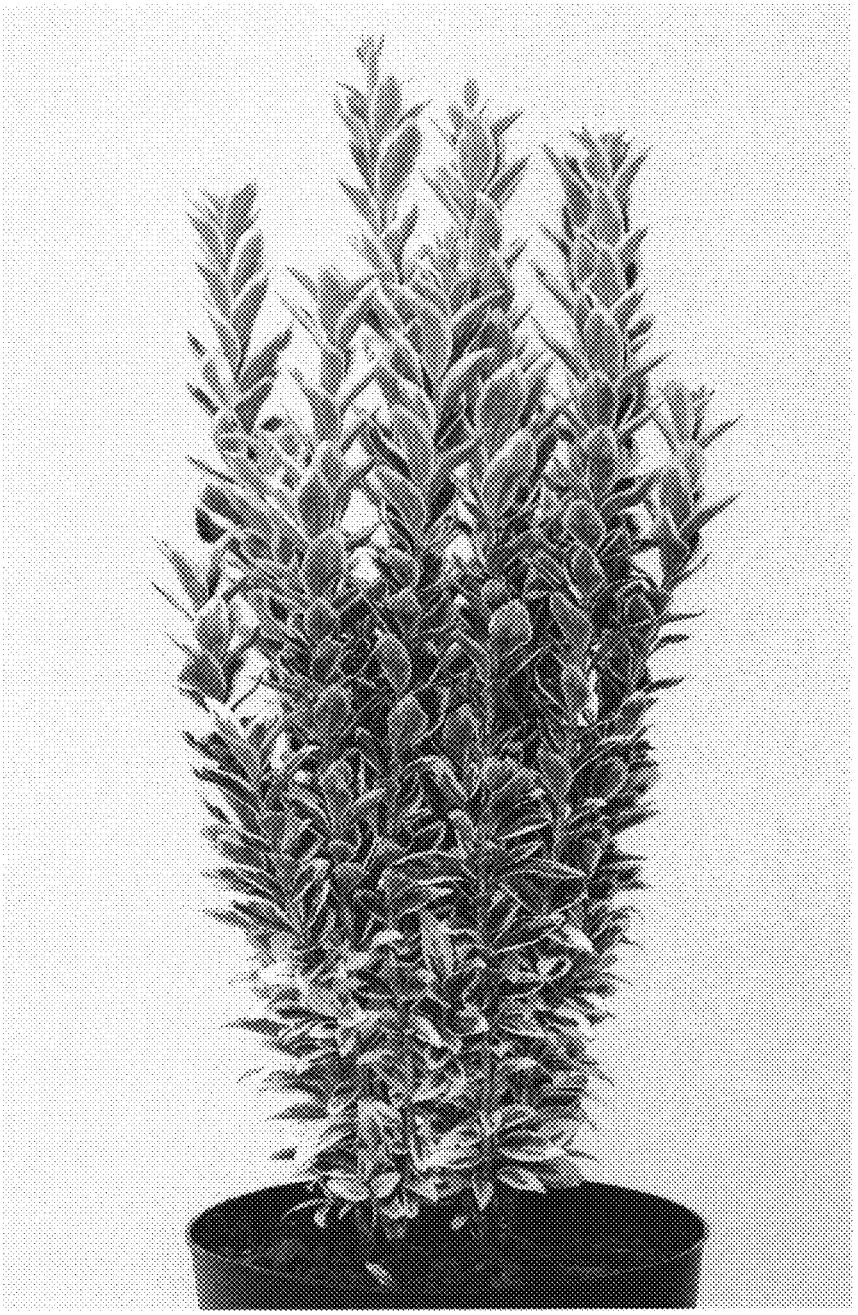

Latin name of the genus and species: *Euonymous japonicus*.

Variety denomination: 'WHITE SPIRE'.

BACKGROUND OF THE INVENTION

The new cultivar is a product of chance discovery by the inventor, at a commercial nursery in St. Oedenrode, The Netherlands, during August of 2012. This new variety, hereinafter referred to as 'WHITE SPIRE', was discovered as a naturally occurring, single branch mutation occurring in an outdoor containerized area, of the parent variety *Euonymous* hybrid, 'Green Spire', unpatented.

After identifying the new variety as a potentially interesting selection, the inventor first organized propagation of 'WHITE SPIRE' by softwood vegetative cuttings in October 2012 at the same commercial nursery in St. Oedenrode, The Netherlands. The inventor continued controlled testing and propagation, assessing stability of the unique characteristics of this variety. Numerous generations have been reproduced and have shown that the unique features of this cultivar are stable and reproduced true to type.

SUMMARY OF THE INVENTION

The cultivar 'WHITE SPIRE' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'WHITE SPIRE' These characteristics in combination distinguish 'WHITE SPIRE' as a new and distinct *Euonymous* cultivar:

1. Stable variegated foliage having green, white, yellow-green, greyed-green and green-white marbling.
2. Upright, dense, neat habit. Overall shape is columnar to broad columnar.
3. Keeps its foliage color well all year round (fades less than other varieties).

COMPARISON TO PARENT VARIETY

*Euonymous* 'WHITE SPIRE' is similar to the parent variety *Euonymous* 'Green Spire' in most horticultural characteristics; however, the new variety differs in the following:

1. The new variety is a smaller plant that the parent.
2. The new variety has variegated foliage, while the parent has fully green foliage.

COMMERCIAL COMPARISON

'WHITE SPIRE' can be compared to the commercial variety *Euonymous japonicus* 'Silver Queen', unpatented. Plants of the new cultivar 'WHITE SPIRE' are similar to plants of 'Silver Queen' in most horticultural characteristics, however, plants of the new cultivar 'WHITE SPIRE' differ in the following:

1. The new variety produces elliptic shaped leaves, this comparator produces ovate leaves.
2. The new variety has a much more upright plant habit than this comparator which is globular.

'WHITE SPIRE' can also be compared to the commercial variety *Euonymous* 'Marieke', unpatented. Plants of the new cultivar 'WHITE SPIRE' are similar to plants of 'Marieke' in most horticultural characteristics, however, plants of the new cultivar 'WHITE SPIRE' differ in the following;

1. 'WHITE SPIRE' has smaller leaves than this comparator.
2. Foliage of the new variety is variegated white, yellow-green, greyed-green, green-white and green marbling, while foliage of this comparator is more green and yellow- green.

BRIEF DESCRIPTION OF THE PHOTOGRAPHS

The accompanying photograph in FIG. 1 illustrates in full color a 2 year old plant of the new variety in a 3 gallon pot.

Figure 2:
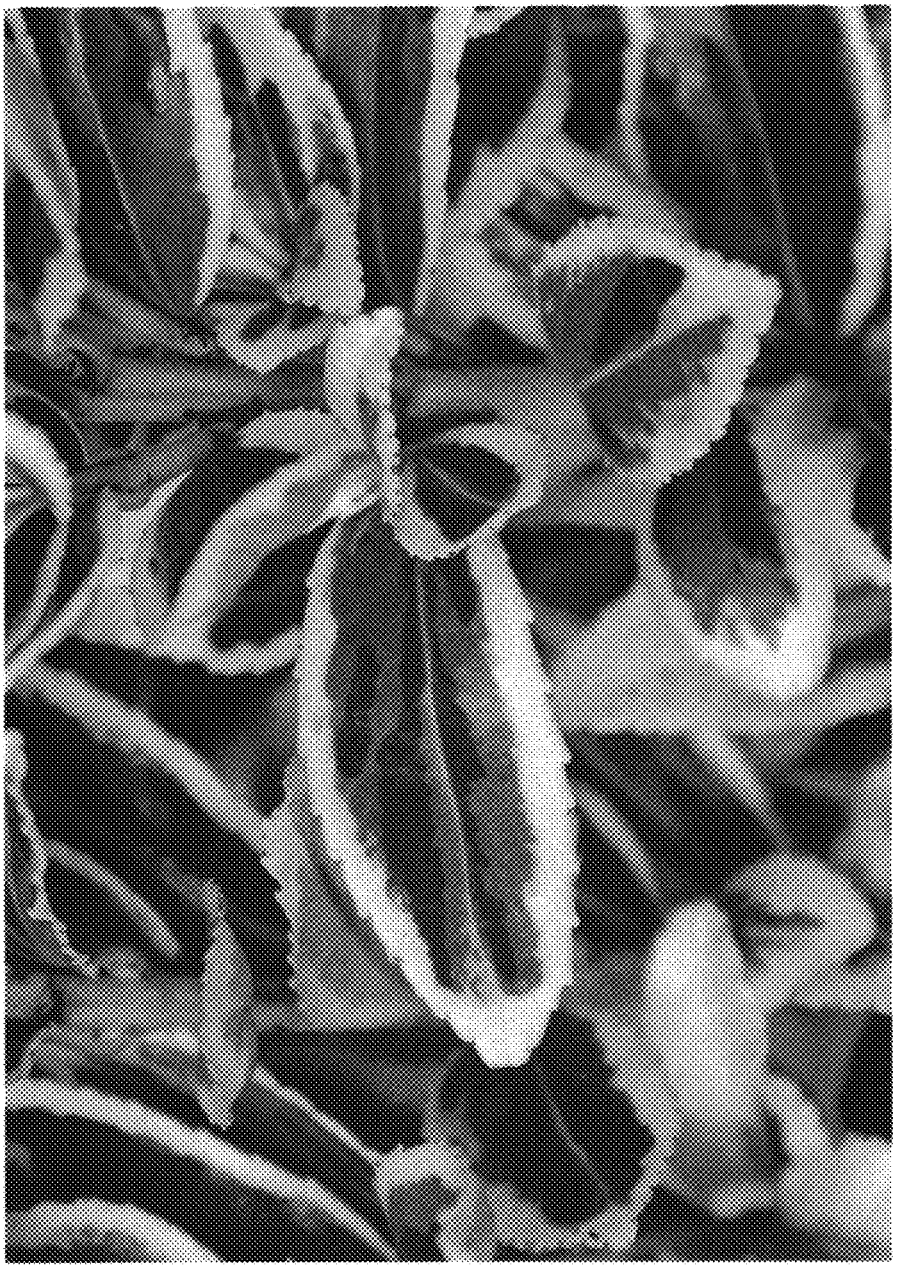

FIG. 2 illustrates a close-up view of the foliage.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'WHITE SPIRE' plants grown outdoors in St. Oedenrode, The Netherlands. Plants are approximately 2 years old, in a 3 gallon nursery container. Measurements and numerical values represent averages of typical plant types.

Botanical classification: *Euonymous japonicus* 'WHITE SPIRE'.

PROPAGATION

Typically by softwood cuttings in Winter.

Root description: Very dense fibrous roots. Colored near RHS Grey-Brown 199C.

PLANT

Growth habit: Perennial evergreen shrub. Narrow, upright. Columnar to broad columnar.

Growth rate: Moderate.

Plant vigor: Moderate to high.

Height: Approximately 39.5 cm.

Plant spread: Approximately 19.8 cm.

Branching characteristics: Main stems grow from the base, with lateral branches.

Main stems:

*Length*.—Average 30.1 cm.

*Diameter*.—Approximately 0.25 cm.

Stems:

*Shape*.—Rounded.

*Luster*.—Matte.

*Aspect*.—85°.

*Strength*.—Strong.

*Color*.—Immature: Near RHS Yellow-Green 144C. Mature: Near RHS Yellow-Green 147C. Older Bark: RHS Greyed-Brown 199A to N199A.

*Texture*.—Glabrous.

Internode length: Average 0.9 cm.

Age of plant described: Approximately 2 years.

FOLIAGE

Leaf:

*Type*.—Single

*Arrangement*.—Opposite.

*Number per lateral branch*.—Average 68 (34 pairs).

*Average length*.—Approximately 3 cm.

*Average width*.—Approximately 1.5 cm.

*Shape of blade*.—Elliptic.

*Apex*.—Bluntly acute.

*Base*.—Attenuate.

*Margin*.—Dentate/crenate.

*Margin undulation*.—Slightly undulate.

*Lobed/unlobed*?.—Unlobed.

*Texture of top surface*.—Glabrous.

*Texture of bottom surface*.—Glabrous.

*Pubescence*.—None.

*Rugosity*.—Non-rugose, both sides.

*Luster*.—Upper side: Moderately glossy. Under side: Matte.

*Color*.—Young foliage upper side: Emerging foliage colored near Yellow 8D, changing to RHS Yellow-Green; 144A to 144B, marbled 146D, margined RHS White 155A and Yellow 4D. Young foliage under side: Emerging foliage colored near Yellow 8D, changing to RHS Yellow-Green; 147D, margined White 155A and Yellow 4D. Mature foliage upper side: RHS Green to Yellow-Green; in between 139A and 147A but slightly darker, marbled Greyed-Green; N189B and N189C, leaf moderately margined White to Green-white; in between 155C and 157D. Mature foliage under side: RHS Greyed-Green; 191A, moderately margined Green White to Yellow; in between 157B and 4D.

*Venation*.—Type: Pinnate. Venation color upper side: RHS Greyed-Green 191B. Venation color under side: RHS Green 137B.

*Petiole*.—Length: About 0.35 cm. Diameter: 0.8 to 1 mm. Texture: Both sides smooth, glabrous. Luster: Bothe sides slightly glossy. Strength: Strong. Color: Upper Surface: RHS Greyed-Green 191C. Lower Surface: RHS Greyed-Green 191B.

FLOWERS AND REPRODUCTIVE ORGANS

Not observed to date.

OTHER CHARACTERISTICS

Disease and pest resistance: Neither resistance nor susceptibility to normal diseases and pests of *Euonymous* observed. Potential insect problems include whitefly and scale. Potential disease problems include leaf spot, and powdery mildew.

Temperature tolerance: USDA zones 6 to 10.

Fruit/seed production: Not observed to date.

What is claimed is:

1. A new and distinct cultivar of *Euonymous* plant named 'WHITE SPIRE' as herein illustrated and described.

* * * * *